United States Patent [19]

DeBusk et al.

[11] Patent Number: 5,344,415
[45] Date of Patent: Sep. 6, 1994

[54] STERILE SYSTEM FOR DRESSING VASCULAR ACCESS SITE

[75] Inventors: Janet S. DeBusk; Margaret M. Felice, both of Knoxville, Tenn.

[73] Assignee: DeRoyal Industries, Inc., Powell, Tenn.

[21] Appl. No.: 77,565

[22] Filed: Jun. 15, 1993

[51] Int. Cl.$^5$ .............................................. A61F 13/00
[52] U.S. Cl. ...................................... 604/304; 604/307
[58] Field of Search ....................... 604/304, 307, 308; 602/53, 57, 56, 58

[56] References Cited

U.S. PATENT DOCUMENTS

| | | | |
|---|---|---|---|
| 4,743,232 | 5/1988 | Kruger | 604/304 |
| 5,230,350 | 7/1993 | Fentress | 604/307 |

*Primary Examiner*—Jerome L. Kruter
*Attorney, Agent, or Firm*—Luedeka, Neely & Graham

[57] ABSTRACT

The specification discloses a sterile system and associated method for dressing vascular access sites in the skin penetrated by needles or catheters. The system includes a sealed container defining a sterile enclosure within which are provided dressing components including a sterile absorbent pad for being adhesively secured over the vascular access site to cover and protect the penetration area and the lead-in portion of the catheter tube, and a sterile adhesive strip for being adhesively secured to the skin of the patient under the tube as it emerges from beneath the pad, and between the skin and the pad along the edges of the pad in opposite directions from the tube exit location. The dressing components cooperate to engage the tube against lateral and longitudinal movement to provide a more secure infusion site. The system as a whole provides a more sterile, reliable and uniform dressing for vascular access sites.

11 Claims, 4 Drawing Sheets

STERILE SYSTEM FOR DRESSING VASCULAR ACCESS SITE

TECHNICAL FIELD

This invention relates generally to the dressing of wounds. More particularly, this invention relates to a sterile system for dressing a vascular access site, such as an intravenous infusion site.

BACKGROUND OF THE INVENTION

It is common in the medical field to introduce treatment substances, such as blood, saline solution, chemotherapy or other drugs into a patient by intravenous infusion methods. These methods generally involve the sterile insertion of a needle or catheter into a vein at a chosen access site and thereafter introducing the treatment substance from a sealed, sterile source into the vein through the needle or catheter.

For example, to insert the catheter, a suitable access site is selected and the skin is cleansed, as by rubbing with isopropyl alcohol, and a needle is first inserted into a vein adjacent the site. The catheter is then threaded through the needle and the needle removed. Alternatively, a catheter having a built in hub and needle cannula may be used, wherein only the cannula penetrates the skin.

The catheter is typically immobilized to reduce damage to the vein and the skin adjacent the access site, avoid unintended displacement of the catheter and to reduce patient discomfort. To avoid bacterial buildup and possible infection, dressings are placed over the catheter insertion site and changed on a frequent basis.

A problem often encountered during the initial installation of the catheter and during changing of the dressing involves the immobilization of the catheter or needle. Normally, the step of dressing the site involves placing an absorbent bandage or gauze pad over the site and securing the gauze in place with waterproof tape. In addition, the tape also helps immobilize the catheter to prevent damage to the site and to reduce patient discomfort. This typically involves surrounding at least a portion of the catheter with tape and attaching the tape to the gauze pad or skin on opposite sides of the catheter. To improve the fit of the tape to the catheter, the tape may be trimmed to an appropriate size during the dressing change and may also be cut with scissors to shape the tape for receiving the catheter.

Case-by-case adaptation of tape and bandages complicates the dressing change procedure and also introduces a possible source of infection, since the tape is usually not sterile and, even if initially sterile, the tape may become contaminated during handling, especially if cut with unsterilized scissors. Changing of the dressing using such methods is therefore often time consuming and difficult to accomplish, since the tape is usually cut on site. In addition, the skill of the medical personnel who apply or change the dressing impacts the quality, sterility and effectiveness of the dressing change, particularly if the tape is cut to fit the catheter.

Accordingly, it is an object of the present invention to provide a sterile system and method for dressing vascular access sites.

Another object of the invention is to provide a system and method for dressing vascular access sites which helps avoid patient discomfort and infection.

It is another object of the invention to provide a system and method of the character described which helps to improve the uniformity of site dressings and lessens the time and skill required to effectively dress a vascular access site in a sterile manner.

A further object of the present invention is to provide a system of the character described which is cost effective and easy to use.

SUMMARY OF THE INVENTION

Having regard to the foregoing and other objects, the present invention is directed to a sterile system and associated method for dressing vascular access sites consisting of an invasive medical device such as a catheter tube or needle entering the body of a patient through a puncture in the skin defining a vascular access site.

According to one aspect of the invention, a system for dressing a vascular access site includes a container defining a sterile enclosure containing a preformed, sterilized dressing. The dressing includes a first dressing component which comprises an absorbent pad dimensioned to substantially cover the access site and adapted to absorb moisture from adjacent the site. The pad has a first surface for being disposed facing toward the site and a second surface for being disposed facing away from the site. A barrier film is disposed adjacent the second surface of the pad and is adapted to limit entry of moisture and bacteria into the pad from the environment while providing a controlled rate of evaporation from the pad. A breathable adhesive-backed web is disposed adjacent the second surface of the pad with the barrier film between the pad and the web. The web extends out from the marginal edge of the pad and the film for adhesively securing the pad against the skin over the access site. A substantially non-adherent material is provided on the first surface of the pad for placement against the skin to limit adhering the pad to skin tissue or exudate adjacent the side. A peel-away cover layer covers at least the portion of the adhesive surface of the web extending out from the pad to provide ready exposure of the adhesive surface of the web by peeling the cover away for attachment of the first dressing component to the skin about the access site.

It will be understood that upon placement of the first dressing component over the site, the catheter or other tube device will emerge from under the edge of the web with the adhesive securement of the web to the skin on opposite sides of the tube pressingly engaging the tube against the skin. However, openings may exist on opposite sides of the tube since the thickness of the tube may raise a portion of the web from the skin and prevent continuous contact between the web and the skin for a short distance to each side of the tube exit location.

A second dressing component within the container includes a breathable, adhesive-backed web having a peel-away cover covering the adhesive surface of the web to provide ready exposure of the adhesive surface by peeling the cover away for attachment of the web to a desired surface. The web of the second dressing component is dimensioned to provide for adhesive securement of a first portion of the web to the skin located beneath the tube adjacent the tube exit location and along the skin extending in opposite directions from the tube exit location, and for adhesive securement of a second portion of the web of the second component to the web of the first dressing component along the marginal edge of the web of the first dressing component adjacent the tube exit location. In this manner, the tube may be engaged between the web of the first dressing component and the web of the second dressing component so that undesired lateral and longitudinal movement of the tube is restricted. Also, any openings on opposite sides of the tube exit location may be substantially covered by extension of the web of the second dressing component between the skin and the raised area of the web of the first dressing component.

In a preferred embodiment, the web of the second dressing component is provided by an elongate strip of breathable material with adhesive along one surface for attachment of the strip to the web of the first dressing component and the skin. The strip includes a notch or indentation along one of its marginal edges, such as a V-shaped cut, which is dimensioned to receive the tube so that the side of the strip generally between the apex of the "V" and the opposite marginal edge may be secured along the length of the strip to the skin beneath the tube and the other side of strip extending longitudinally from opposite ends of the "V" opening may be secured to the web of the first dressing component.

It will be appreciated that the invention addresses and overcomes significant problems and inconveniences associated with the dressing of vascular access sites. A self-contained ready-to-use sterile vascular access dressing according to the invention affords many advantages over prior methods and techniques including in particular, reliability, uniformity, and reduction in labor and skill requirements associated with conventional methods.

BRIEF DESCRIPTION OF THE DRAWINGS

The above and other features and advantages of the present invention will become further known from the following detailed description when considered in conjunction with the accompanying drawings in which:

FIG. 5a is an enlarged cross-sectional view taken along line 5a—5a of FIG. 5;

DETAILED DESCRIPTION OF A PREFERRED EMBODIMENT

Figure 1:
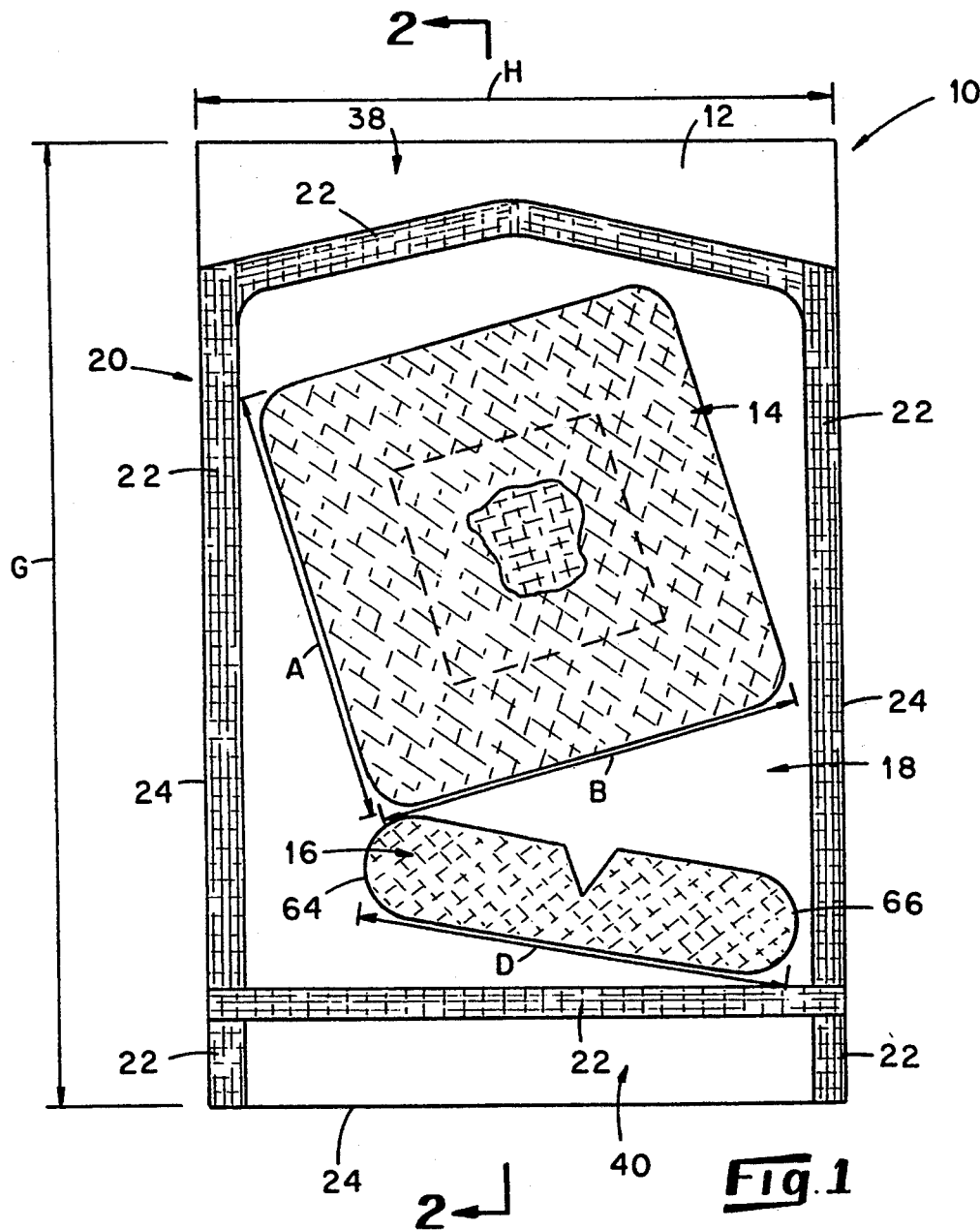
FIG. 1 is a top plan view of a sterile system for dressing vascular access sites in accordance with a preferred embodiment of the present invention.

With reference now to FIG. 1, there is shown a sterile system 10 in accordance with a preferred embodiment of the present invention for dressing vascular access sites. The system 10 includes a sealed package or container 12 containing at least a first sterile dressing component in the form of a sterile site-covering pad 14 and a second sterile dressing component in the form of a sterile immobilizing strip 16.

As will be described in more detail hereinafter, the pad 14 and the strip 16 are confined within a sterile enclosure 18 of container 12 to isolate the components from the environment and other sources of contamination and maintain the sterility of the components until they are ready for use. The boundaries of the enclosure 18 in the illustrated embodiment are defined by a continuous seal 20 provided by a series of interconnected weld paths 22 located on the container 12 generally between the enclosure 18 and an outer periphery 24 of the container 12.

The pad 14 and strip 16 are provided by materials suitable for use in the dressing of wounds, such as vascular access sites of the type commonly encountered in the administration of substances by intravenous infusion. The pad 14 and strip 16 are pre-preformed and ready for immediate use to allow quick and uniform dressing of wounds and thus use of the system enables the user to avoid the need to cut or otherwise shape the dressing components on-site. In addition, the system 10 provides the sterile pad 14 and strip 16 in a sterile enclosure 18 and thus provides the pad 14 and strip 16 to medical personnel in a totally sterile condition so that the risk of infection associated with conventional completed dressings is markedly reduced.

Figure 2:
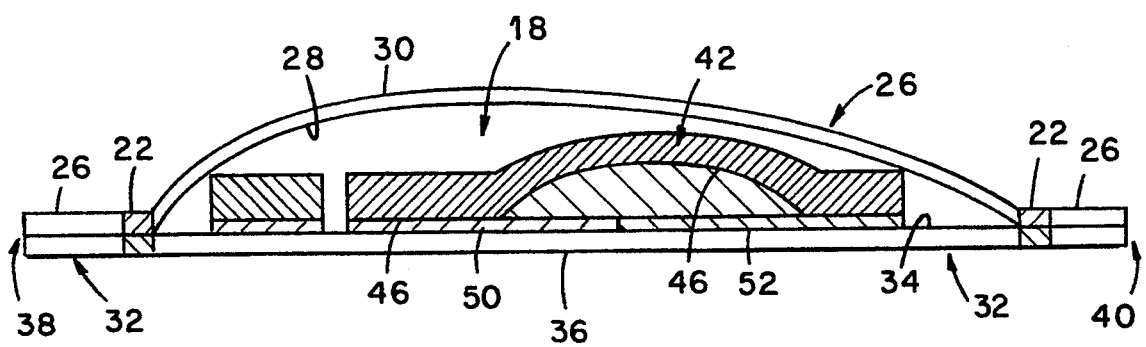
FIG. 2 is an enlarged cross-sectional view taken along line 2—2 of FIG. 1.

Turning to FIG. 2, the container 12 is preferably rectangular, flat and relatively thin for ease of handling and storage and is provided by a top sheet or layer 26, preferably a sterilizable sheet of clear plastic material so that the contents may be viewed. The layer 26 may be provided by the polyethylene coated polyester film available from Hargro Flexible Packaging of Edinburgh, Ind., under the product designation "CT 205E". The layer 26 has a sterile inner surface 28 and an outer surface 30.

The enclosure 12 further includes a bottom sheet or layer 32, preferably a sterilizable sheet of a printable, opaque plastic or composite material having dimensions identical to those of the top layer, such as the polyester/polyethylene sheet material available from The DuPont Company of Wilmington, Del. under the trademark TYVEK, to define a sterile inner surface 34 and an exterior surface 36.

The seal 20 of the container 12 is preferably formed by heat sealing the top layer 26 to the bottom layer 32 along the weld paths 22.

The container 12 is preferably assembled by placing the pad 14 and strip 16 in a flat orientation or the inner surface 34 of the bottom layer 32 at a location intermediate the intended location of the weld paths 22. The inner surface 30 of the top layer 26 is then placed over the pad 14 and strip 16 and the inner surface 34 of the bottom layer 32 with the boundary or marginal edges of layers 26 and 32 in alignment, and the seal 20 is accomplished by application of heat and pressure or other suitable sealing method along the weld paths 22 to fuse the portions of the top and bottom layers together in the vicinity of the weld paths 22. In addition, mutually facing portions of the top and bottom layers located outwardly of the weld paths 22 (indicated generally as areas 38 and 40) may be releasably adhered to one another, such as by adhesive, to provide reclosable access ports, the purpose of which will be explained more fully below.

It is believed that persons of ordinary skill will be familiar with conventional methods of assembling sterile packages by various known processes. However, a preferred method of sterilization of the container 12 and its contents involves sterilization of the assembled container 12 using the ethylene oxide process after the container is sealed. In this process, sterilization of the sealed container is preceded by a preconditioning phase. The container 12 is conditioned at a temperature between 90° to 120° F. and a relative humidity of 50% to 80% for a time sufficient to bring the internal temperature and humidity of the container to a desired level (minimum normally 12 hours).

After preconditioning, the container 12 is moved directly into a sterilization chamber for gas exposure. The chamber undergoes a vacuum evacuation followed by a leak test. Thereafter, ethylene oxide is introduced into the sterilization chamber to a predetermined pressure and maintained at that pressure for the time required to sterilize the product (average four hours) by diffusion of ethylene oxide molecules through the layers 26 and 32 which, when inside, penetrate the structure of the components 14 and 16 and the interior of the container to effect sterilization of the material. The exposure phase is followed by a series of evacuations and air washes to remove the ethylene oxide from the chamber and the container 12. The container 12 is then placed in degas cells where aeration takes place at an elevated temperature (100° to 140° F.) for a time necessary to bring any ethylene oxide residual levels down to safe handling levels.

Figure 3:
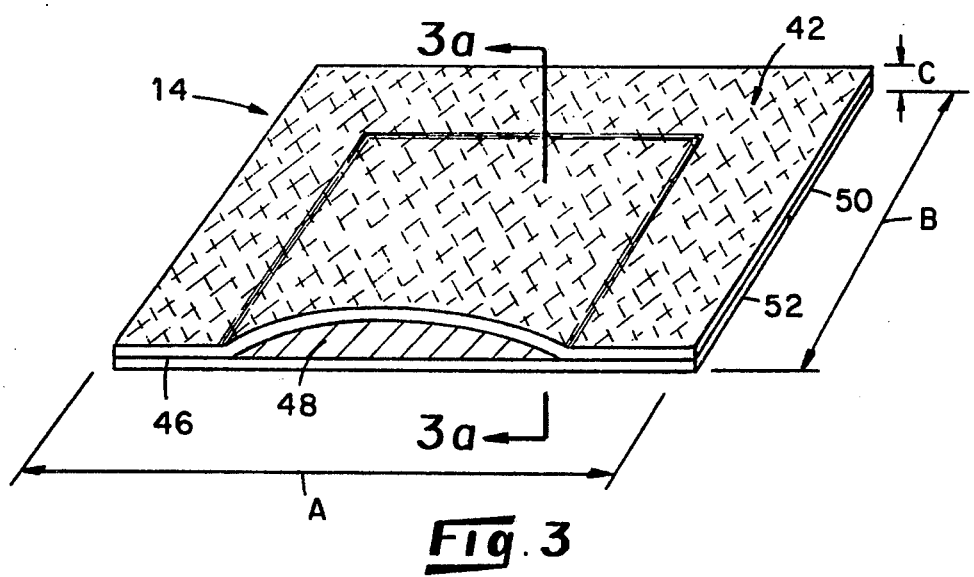
FIG. 3 is an enlarged, partial-perspective view of a sterile pad for use in the system of FIG. 1.
Figure 3A:
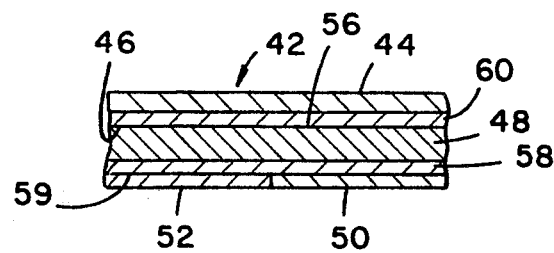
FIG. 3a is an enlarged cross-sectional view taken along line 3a—3a of FIG. 3.

With continuing reference to FIG. 2 and additional reference to FIGS. 3 and 3a, the pad 14 includes a preferably flexible, breathable and conformable web 42 having an adhesive coated lower surface 46, an absorbent medium or pad 48, and removable or peel-back cover strips 50 and 52 for covering the adhesive surface 46 of the web 42 until the pad 14 is ready to secure to the patient.

The web 42 is preferably provided by a fabric of high permeability suitable for medical uses in gauze coverings and the like, such as the nonwoven polypropylene fabric sold by the DuPont Company of Wilmington, Del., under the trademark SONTARA 8010. The web 42 is coated on its surface 43 with a suitable medical grade adhesive such as the polyacrylate adhesive available from Medco Corp. of Bedford, Ohio under the trade designation "Formula No. 60". The web 42 is preferably square with rounded corners as shown, but may be provided in other shapes depending on the intended use.

The absorbent pad 48 is preferably provided by a soft, absorbent rayon or cotton material such as multi-layer gauze or batting for covering the access site, absorbing drainage and moisture from adjacent the access site and for helping to keep sutures such as the relatively stiff, protruding nylon sutures from breaking through the dressing provided by the pad 14 and strip 16. The absorbent pad 48 preferably has a substantially uniform thickness substantially greater than that of the web 42 and is centered on the web as shown.

The absorbent pad 48 has an upper surface 56 for facing away from the access site and a lower surface 58 for facing toward the site. The lower surface 58 is preferably laminated with a non-adherent wound contact medium 59, such as the polyethylene netting available from Applied Extrusion Technologies of Middletown, Del., under the trademark DELNET, to directly cover and protect the access site.

A substantially transparent barrier layer 60, such as a nonocclusive polyurethane film available from Medco of Bedford, Ohio under the trademark product No. 8108 is attached, as by a coating of a suitable medical adhesive, to the upper surface 56 of the absorbent pad 48. In a preferred embodiment, the barrier layer 60 provides a barrier to external contaminants, restricts drainage strike-through, helps maintain a desirable moist environment and allows for controlled vapor transmission out of the wound area.

It is a feature of the invention that the barrier layer 60 may only extend over the pad 48, and not into regions of the web 42 extending outwardly from the pad. While the barrier layer 60 permits a degree of evaporation from the pad, it is not believed to be of sufficient vapor transmissibility to function comfortably when applied directly to the skin. In this regard, it is noted that a prior practice has been to apply such a film to the skin directly over an access site to hold down a tube against the skin. This film of limited "breathability" is uncomfortable and may lead to blistering adjacent the site.

Figure 4:
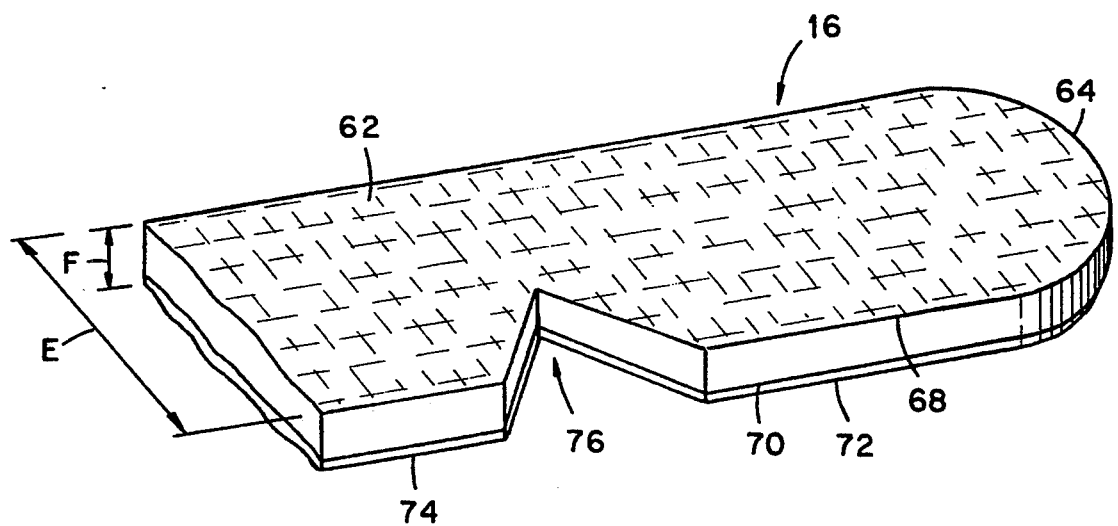
FIG. 4 is an enlarged perspective view in cross-section of an immobilizing strip for use in the system of FIG. 1.

With reference now to FIG. 4, the strip 16 is preferably provided by a flexible, breathable and conformable web 62, elongate in configuration, having rounded opposite ends 64 and 66, a textured upper surface 68 and an adhesive coated lower surface 70. The web 62 may be, and preferably is, provided by the same material as the material of construction of the web 42. Removable cover or peel-back strips 72 and 74 contact the lower surface 70 and isolate the adhesive of the tape 62 from contact with the container 12 of other surfaces until the strip is ready to be secured in place adjacent the access site.

In a preferred embodiment, the strip 16 includes a notch or indent such as, for example, a generally V-shaped cutout 76 positioned along one of its marginal edges dimensioned to engage a catheter 78, shown in FIG. 5, as will be explained more fully below.

The following dimensions are provided as an example of a system suitable for dressing commonly encountered access sites. However, it will be understood that the system 10 may be provided in virtually any size. Continuing with the example, the pad 14 may have a length A of about 4 inches and a width B of about 4 inches. The web 42 may have a thickness of about 1/32 of an inch and the absorbent medium may have a thickness of about 1/16 of an inch. The strip 16 may have a length D of about 4 inches, a width E of about 1 inch and a thickness F of about 1/32 of an inch. The notch 72 may have a depth of about ½ inch and be located an equal distance from the ends 64 and 66. The angle between opposite sides of the U-shaped notch is preferably about 50 degrees.

When used with these pad and strip dimensions, the top layer 28 and the bottom layer 32 of the container 12 may each have a length G of about 9 inches, a width H of about 6 inches and a thickness (not shown) of about 1/64 of an inch.

Figure 5:
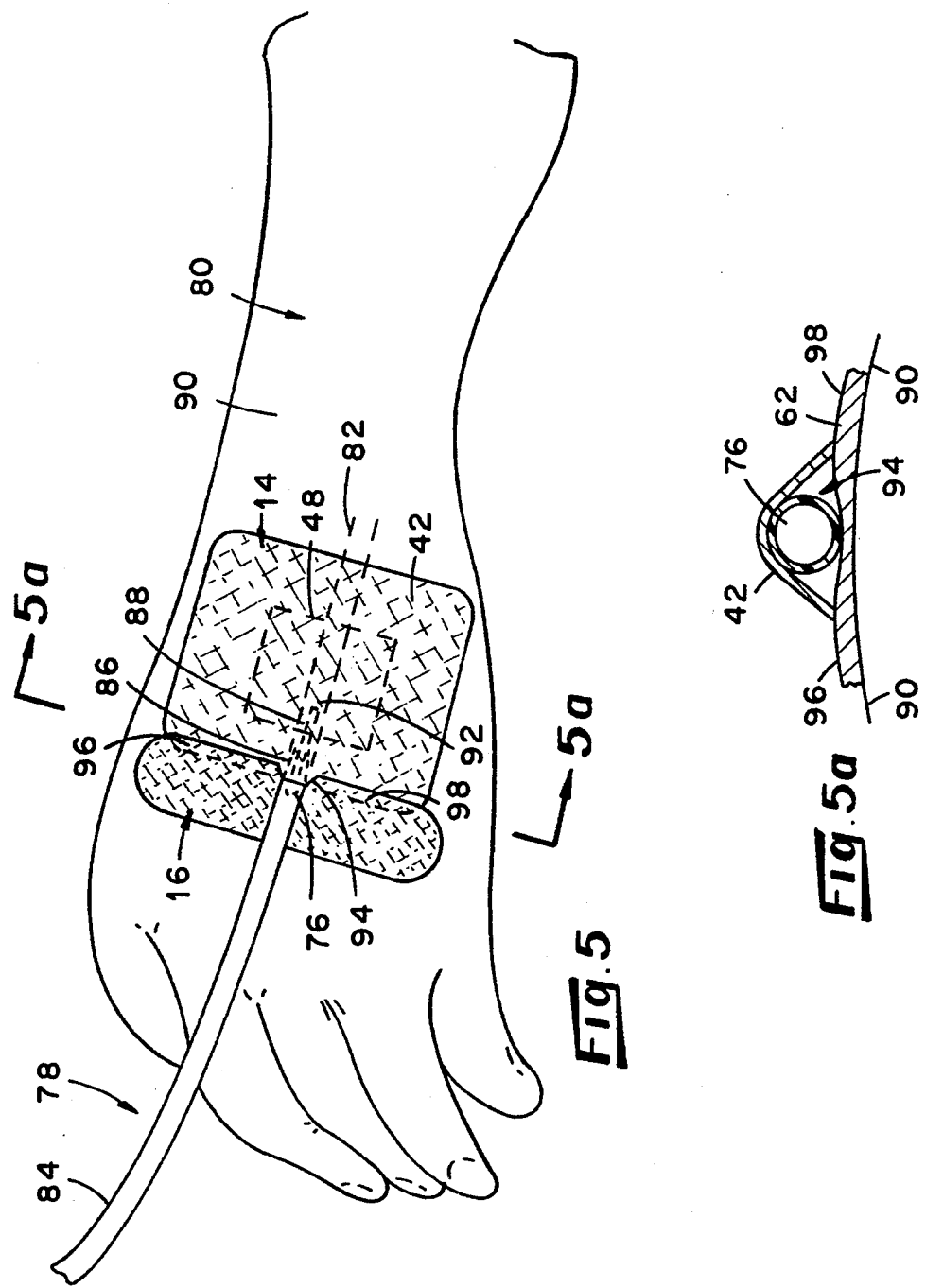
FIG. 5 is a perspective view showing components of the system of FIG. 1 installed on a patient's arm as a dressing for a vascular access site.

With reference now to FIG. 5, there is shown an arm 80 of a patient which has been penetrated with an invasive medical device such as a catheter 78 for infusion of a medical treatment substance, such as saline solution, chemotherapy drugs or blood, for example into a vein 82 of the patient. However, it will be appreciated that the system of the invention may be used for dressing any tubular entry site in addition to a vascular access site such as an abdominal port for supplying fluids to or removing fluids from adjacent various organs or body cavities.

The catheter 78 of the illustration includes a catheter tube 84 in flow communication with a hub 86 and a needle cannula 88. The needle cannula 88 penetrates skin 90 and vein 82 of the patient adjacent an access site 92 to provide a direct pathway from the vein 82 to the catheter tube 84 and enable the infusion of medical treatment substances into the patient's bloodstream.

In use of the system 10 of the invention, the seal of the container 12 is broken to obtain access to the pad 14 and the strip 16 for removal from the enclosure 18. This is preferably accomplished by grasping the top layer 26 and the bottom layer of the container 12 adjacent the area 38 and/or the area 40 and pulling the top and bottom to separate the seal 20 along the weld paths 22 adjacent the area 38 and/or 40 to provide access to the enclosure 18 for removal of the contents. After changing a dressing, used dressing constituents may be inserted into the empty container 12 through the area 38 or 40 and the area 38 and/or 40 may be re-closed by application of low pressure to reinstitute the seal attributable to the presence of adhesive between the top and bottom layers in these areas. In this manner, used constituents may be isolated for disposal to help avoid the spread of infection.

After the pad 14 and strip 16 are removed from the sterile enclosure, the pad 14 is first positioned over the access site and the strip 16 is then positioned relative to the pad 14 and the catheter to further immobilize the catheter and shield the access site from the environment. To this end, the pad is prepared for application by removing the cover strips 50 and 52. The pad 14 is then placed down onto the site 92 so that the pad 14 covers a portion of the catheter and the pad 48 is substantially centered over the site, with the adhesive surface 46 in contact with the skin 90 of the patient's arm 80 about the site to hold the pad 14 against the skin and against the lead-in portion of the catheter which is underneath the pad 14.

The adhesive engagement of pad 14 to the skin in this manner causes the catheter to be pressingly engaged against the skin as it emerges from beneath the edge of the web of the pad at a catheter exit location 94, as shown in FIG. 5a. Thus, with reference to FIG. 5a, it will be seen that upon placement of the pad 14 over the site, the catheter will extend from under the edge of the web 42 with the adhesive surface 46 of the web 42 on opposite sides of the catheter pressingly engaging the catheter 78 against the skin 90. However, openings may exist on opposite sides of the catheter since the thickness of the catheter may tend to lift the web from the skin adjacent the catheter and interrupt continuous contact between the web and the skin for a distance to each side of the exit location 94.

To complete installation of the dressing, the cover strips 70 and 72 are removed from the adhesive surface 70 of the strip 16 and the strip 16 is positioned between the tube 84 of the catheter 78 and the skin 90 of the patient's arm 80, with the notch 76 receiving the hub 86 of the catheter. Peripheral or marginal edge regions 96 and 98 of the adhesive surface 70 are positioned to overlap and adhesively secure the strip 16 to the upper surface 44 of the pad 14 on opposite sides of the hub 86 of catheter 78, with remaining portions of the adhesive surface 70 adhesively securing the strip 16 to the skin 90 of the user's arm 80.

The web 62 of the strip 16 is therefore dimensioned to provide for adhesive securement of a first portion of the web to the skin located beneath the catheter 78 adjacent the exit location 94 and extending out along opposite directions from the exit location, and adhesive securement of a second portion of the web 62 of the strip 16 to the web 42 of the pad 14 along the marginal edge of the web 42 immediately adjacent the exit location 94. In this manner, the catheter is engaged between the web 42 of the pad 14 and the web 62 of the strip 16 as by receipt of the hub or tube within the notch 76 so that undesired lateral and longitudinal movement of the catheter is restricted. Also, the openings which existed on opposite sides of the exit location due to the raising up of the web 42 of the pad 14 are substantially covered since the web 62 of the strip 16 spans across the openings between the skin and the raised area of the web 42 of the pad 14 adjacent the exit location 94, as best seen in FIG. 5a.

Accordingly, it will be understood that once installed, the dressing provided by the pad 14 and the strip 16 serves to protect the access site from infection and damage. The dressing acts as a barrier to inhibit external infectious or infection-promoting constituents from reaching the access site. In addition, the components of the dressing help to protect the access site from damage and provide desirable control of moisture transmission from coverage areas, and the combination of the immobilizing strip with the pad helps to immobilize the catheter to reduce patient discomfort and to prevent damage to the vein and the access site from movement of the catheter relative to the access site.

As described above, the pad 14 and strip 16 are pre-formed and configured to allow quick and uniform dressing of wounds and thus use of the system enables the user to avoid the need to cut or otherwise shape the dressing components on-site. In addition, the system 10 provides the sterile pad 14 and mobilizer 16 in a sterile enclosure 12 so that the pad 14 and strip 16 are available to medical personnel in a sterile condition for immediate use to reduce the risk of infection associated with conventional dressings and dressing methods.

Figure 6:
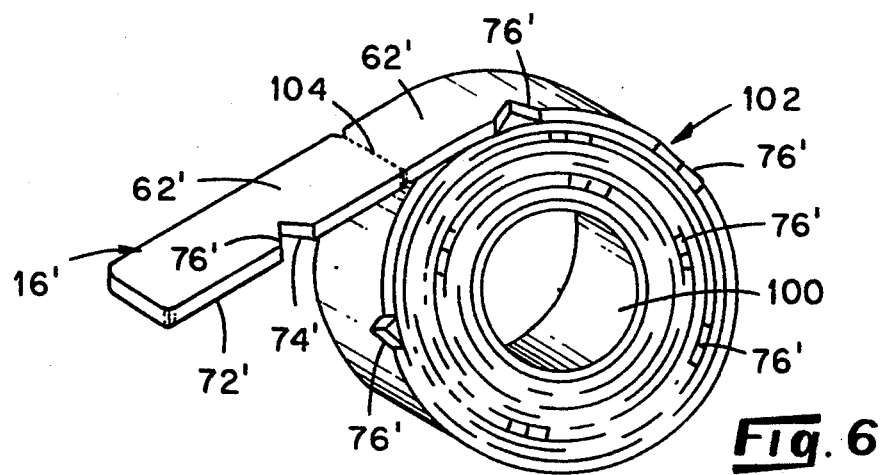
FIG. 6 is a perspective view showing a roll of preformed strips for providing a component of a vascular access dressing according to one embodiment of the invention.

With reference to FIG. 6, it will be seen that the strip 16 of the system 10 may be supplied from a series of individual strips 16' connected end-to-end and wound on a plastic or paper tubular core 100 of a roll 102. Score lines 104 demark the location of the separation between adjacent strips 16 and provide easy separation of strips from the roll.

Figure 7:
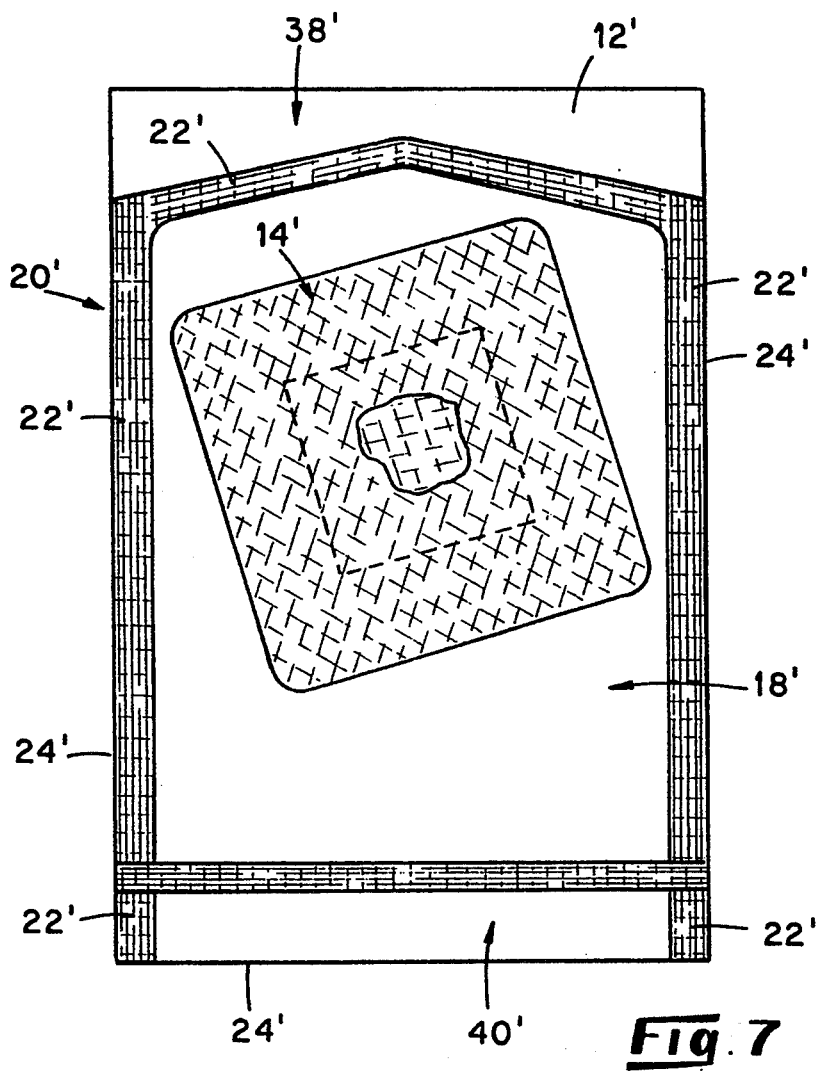
FIG. 7 is a top plan view of an alternate embodiment of the system of FIG. 1.

It will further be appreciated that the strip 16 may be provided pre-formed on site as from roll 102 together with a sterile dressing component 14' in a system 10' of FIG. 7, with the reference characters corresponding to those of FIGS. 1–5 designated by a prime suffix. The system of FIG. 7 thus includes at least the one sterile dressing component 14' with pre-formed dressing component 16' supplied as from roll 102.

The foregoing description of certain embodiments of the present invention has been provided for purposes of illustration only, and it is understood that numerous modifications or alterations may be made without departing from the spirit and scope of the invention as defined in the following claims.

We claim:

1. A system for dressing a tubular access site adjacent the skin of a patient penetrated by an invasive medical device such as a catheter tube, said system comprising:
   a container defining a sterile, sealed enclosure therein; and a preformed, sterilized dressing located within said enclosure, said dressing comprising:

a first sterile dressing component comprising an absorbent pad dimensioned to substantially cover the access site and adapted to absorb fluid from adjacent the access site, said absorbent pad having a first surface for being disposed adjacent the site and a second surface for being disposed facing away from the site, a breathable adhesive-backed web disposed adjacent said second surface of said pad and extending out from a marginal edge of said pad for adhesively securing said pad to the skin around the access site, a barrier film disposed adjacent said second surface of said pad intermediate said pad and said web and adapted to limit entry of moisture and bacteria into said pad from the environment while providing a controlled rate of evaporation of fluids from said pad, a substantially non-adherent covering disposed adjacent said first surface of pad to be placed against the skin to limit adherence of said pad to skin tissue or exudate adjacent the site, and a peel-away cover layer covering at least the portion of said adhesive surface of said web extending out from said pad to provide ready exposure of said adhesive surface of said web by peeling said cover away for attachment of said first dressing component to the skin about the access site, wherein when said first component may be placed over the access site such that a portion of said web will overlay the catheter tube and thereby define a catheter exit location at which the catheter tube is engaged between said web and the skin; and a second sterile dressing component comprising a breathable web having an adhesive surface and a peel-away cover covering said adhesive surface of said web to provide ready exposure of said adhesive surface by peeling said cover away for attachment of said web of said second sterile dressing component to a desired surface, said web of said second dressing component being dimensioned to provide adhesive securement of a first portion of said web to the skin of the user beneath the catheter tube adjacent the catheter exit location and extending out along opposite directions from the exit location, and to provide adhesive securement of a second portion of said web of said second component to said web of the first dressing component along the marginal edge of said web of said first dressing component adjacent the exit location, wherein the catheter tube may be engaged between said web of said first dressing component and said web of said second dressing component so that undesired lateral and longitudinal movement of the tube may be restricted.

2. The system of claim 1, wherein said enclosure comprises a top layer provided by a sterilizable sheet of a transparent plastic material heat sealed along a weld path to a bottom layer provided by a sterilizable sheet of a printable, opaque plastic material.

3. The system of claim 2, wherein said top layer includes an inner surface and said bottom layer includes an inner surface facing the inner surface of the top layer.

4. The system of claim 3, wherein said enclosure is defined between said inner surfaces of said top and bottom layers.

5. The system of claim 1, wherein said first component is separate from said second component.

6. The system of claim 1, further comprising a notch provided on a portion of said web of said second component.

7. The system of claim 1, wherein said second component is an elongate adhesive-backed strip having a V-shaped notch in a marginal edge of said strip about midway along the length of said strip.

8. A system for dressing a tubular access site in the skin of a patient penetrated by a tubular medical device, said system comprising:

a container defining a sterile enclosure;

a first sterile dressing component located within said sterile enclosure, said first sterile dressing component comprising an absorbent pad dimensioned to substantially cover the access site and adapted to absorb fluid from adjacent the access site, said absorbent pad having a first surface for being disposed adjacent the site and a second surface for being disposed facing away from the site, a barrier film disposed adjacent said second surface of said pad and adapted to limit entry of moisture and bacteria into the pad from the environment while providing a controlled rate of evaporation of fluids from said pad, a substantially non-adherent covering disposed adjacent said first surface of said pad to be placed against the skin to limit adherence of said pad to skin tissue or exudate adjacent the site, and a peel-away cover layer covering at least a portion of said adhesive surface of said web extending out from said pad to provide ready exposure of said adhesive surface of said web by peeling said cover away for attachment of said first dressing opponent to the skin about the access site; and a second sterile dressing opponent located within said sterile enclosure, said second sterile dressing component comprising an adhesive-backed breathable web having a peel-away cover layer releasably adhered to the adhesive surface of said web, said web of said second sterile dressing having a marginal edge with a notch provided therein dimensioned to engagingly receive the tubular medical device therein adjacent the access site.

9. The system of claim 8, wherein said web of said second sterile dressing component comprises an elongate strip of generally uniform width and generally parallel marginal edges running the length thereof with said notch having a generally V-shape and being located about midway between the ends of said strip along one of said marginal edges.

10. A method of dressing a tubular access site adjacent the skin of a patient penetrated by a tubular medical device which comprises:

providing a self-contained system for dressing the tubular access site, the system comprising a container defining a sterile, sealed enclosure therein containing a first sterile dressing component comprising an absorbent pad dimensioned to substantially cover the access site and adapted to absorb fluid from adjacent the access site, said absorbent pad having a first surface for being disposed adjacent the site and a second surface for being disposed facing away from the site, a barrier film disposed adjacent the second surface of the pad and adapted to limit entry of moisture and bacteria into the pad from the environment while providing a controlled rate of evaporation of fluids from the pad, a substantially non-adherent covering disposed adjacent the first surface of the pad to be placed against the skin to limit adherence of the pad to skin tissue and exudate adjacent the site, and a peel-away cover layer covering at least a portion of the adhesive surface of the web extending out from the pad to provide ready exposure of the adhesive surface of the web by peeling the cover away for attachment of the first dressing component to the skin about the access site; and a second sterile dressing component comprising an adhesive-backed breathable web having a peel-away cover layer releasably adhered to the adhesive surface of the web, the web of the second sterile dressing component having a marginal edge with an indentation dimensioned to engagingly receive the tube therein;

opening the container to gain access to the first and second sterile dressing components within the enclosure;

removing the first sterile dressing component from the enclosure;

peeling away the peel-away cover layer from the first sterile dressing component to expose the adhesive surface of the web of the first sterile dressing component;

adhesively securing the web of the first sterile dressing component to the skin of the patient with the pad pressingly engaged upon the tube at the site of penetration to substantially cover the site and the portion of the medical device penetrating the site with the adhesive surface of the web of the first dressing component generally sealingly encircling the site and pressingly engaging the portion of the tube leading from the penetration site against the skin so that the tube emerges from beneath a marginal edge of the web at a tube exit location and is engaged between the web of the first dressing component and the skin at the tube exit location;

removing the second sterile dressing component from the enclosure;

peeling away the peel-away cover from the second sterile dressing component and adhesively securing a section of a first portion of the web of the second dressing component to the skin of the user beneath the tube adjacent the tube exit location and securing an additional section of the first portion of the web of the second dressing component to the skin out along opposite directions from the tube exit location; and adhesively securing a second portion of the web of the second dressing component to the web of the first dressing component along a marginal edge of the web of the first dressing component adjacent the tube exit location to engage the tube between the web of the first dressing component and the web of the second dressing component so that undesired lateral and longitudinal movement of the tube is restricted.

11. The method of claim 10, further comprising placing used first and second dressing components within the enclosure of the container after removal of the first and second sterile dressing components therefrom and thereafter closing the enclosure to substantially sealably enclose the used first and second dressing components therein for disposal.

* * * * *

UNITED STATES PATENT AND TRADEMARK OFFICE
CERTIFICATE OF CORRECTION

PATENT NO. : 5,344,415
DATED : September 6, 1994
INVENTOR(S) : Janet S. DeBusk et al.

It is certified that error appears in the above-indentified patent and that said Letters Patent is hereby corrected as shown below:

Column 4, line 53 after "inner" delete "surface 30" and insert --surface 28--

Column 5, line 34 after "having" and before "an" insert --an upper surface 44--

Column 5, line 44 after "its" delete "surface 43" and insert --surface 46--

Column 6, line 56 after "top" delete "layer 28" and insert --layer 26--

UNITED STATES PATENT AND TRADEMARK OFFICE
CERTIFICATE OF CORRECTION

PATENT NO. : 5,344,415
DATED : September 6, 1994
INVENTOR(S) : Janet S. DeBusk, et. al.

It is certified that error appears in the above-indentified patent and that said Letters Patent is hereby corrected as shown below:

<u>Column 7, line 58</u> after "strips" delete "70 and 72" and insert --74 and 72--

Signed and Sealed this

Fourteenth Day of February, 1995

Attest:

BRUCE LEHMAN

Attesting Officer     Commissioner of Patents and Trademarks